(12) United States Patent
Lorenzo

(10) Patent No.: US 8,932,318 B2
(45) Date of Patent: Jan. 13, 2015

(54) EMBOLIC COIL DETACHMENT MECHANISM WITH POLYMER TETHER

(75) Inventor: Juan A. Lorenzo, Davie, FL (US)

(73) Assignee: Depuy Synthes Products, LLC, Raynham, MA (US)

(*) Notice: Subject to any disclaimer, the term of this patent is extended or adjusted under 35 U.S.C. 154(b) by 79 days.

(21) Appl. No.: 13/436,236

(22) Filed: Mar. 30, 2012

(65) Prior Publication Data

US 2013/0261656 A1 Oct. 3, 2013

(51) Int. Cl.
*A61M 29/00* (2006.01)

(52) U.S. Cl.
USPC ............................... 606/200; 606/191

(58) Field of Classification Search
USPC ................................... 606/200, 191
See application file for complete search history.

(56) References Cited

U.S. PATENT DOCUMENTS

| | | | |
|---|---|---|---|
| 5,578,074 A | 11/1996 | Mirigian | |
| 5,911,737 A | 6/1999 | Lee et al. | |
| 5,989,242 A | 11/1999 | Saadat et al. | |
| 6,059,815 A | 5/2000 | Lee et al. | |
| 6,102,933 A | 8/2000 | Lee et al. | |
| 6,575,965 B1 | 6/2003 | Fitch et al. | |
| 6,743,236 B2 | 6/2004 | Barry et al. | |
| 7,578,826 B2 | 8/2009 | Gandhi et al. | |
| 7,582,101 B2 | 9/2009 | Jones et al. | |
| 7,591,833 B2 | 9/2009 | Jones et al. | |
| 7,744,604 B2 | 6/2010 | Maitland et al. | |
| 7,776,054 B2 | 8/2010 | Gandhi et al. | |
| 7,780,680 B2 | 8/2010 | Gandhi et al. | |
| 7,972,342 B2 | 7/2011 | Gandhi et al. | |
| 2001/0029352 A1 | 10/2001 | Gandhi | |
| 2004/0002732 A1* | 1/2004 | Teoh et al. | 606/200 |
| 2005/0043755 A1 | 2/2005 | Wilson | |
| 2006/0025801 A1 | 2/2006 | Lulo et al. | |

(Continued)

FOREIGN PATENT DOCUMENTS

| | | |
|---|---|---|
| EP | 717969 A2 | 6/1996 |
| EP | 717969 A3 | 6/1996 |

(Continued)

OTHER PUBLICATIONS

EPO, Partial European Search Report in European Patent Application No. EP 13152032 mailed Jul. 10, 2013.

(Continued)

*Primary Examiner* — Katherine Dowe
*Assistant Examiner* — Michael Mendoza

(57) ABSTRACT

Provided herein are a system and method for detaching a therapeutic device, e.g. an embolic coil, from a delivery tube at a target site in a patient's body. The system includes a bead disposed against a distal end of the therapeutic device that retains the therapeutic device to the delivery tube in a first compressed configuration through a series of connectors. The series of connectors include a stretch resistant member through which the bead is attached to an anchor inside the therapeutic device. The anchor, in turn, is disposed against a thermally responsive element comprised of a polymeric material configured to melt or otherwise change configuration to release the anchor, and with it, to also release the bead and therapeutic device. Energy may be supplied to the thermally responsive element through electrical conductors and a resistive heating element disposed within the delivery tube.

6 Claims, 2 Drawing Sheets

(56) References Cited

U.S. PATENT DOCUMENTS

| | | |
|---|---|---|
| 2006/0135986 A1 | 6/2006 | Wallace et al. |
| 2006/0271097 A1 | 11/2006 | Ramzipoor et al. |
| 2007/0167911 A1 | 7/2007 | Gandhi |
| 2010/0160944 A1 | 6/2010 | Teoh et al. |
| 2010/0256666 A1* | 10/2010 | Chen et al. .................... 606/191 |
| 2011/0301686 A1 | 12/2011 | Bowman |

FOREIGN PATENT DOCUMENTS

| | | |
|---|---|---|
| WO | 2008144587 A2 | 11/2008 |
| WO | 2011130081 A1 | 10/2011 |

OTHER PUBLICATIONS

European Patent Application No. 14162781.0 Search Report dated Jul. 25, 2014.

* cited by examiner

EMBOLIC COIL DETACHMENT MECHANISM WITH POLYMER TETHER

BACKGROUND

The present invention relates to a medical device for placing an embolic coil at a preselected location within a vessel of the human body, and more particularly, relates to a flexible delivery member having a heating element and a polymer tether member at the distal tip of the delivery member for holding the embolic coil in order to transport the coil to a desired position within the vessel and release the embolic coil at that position.

For many years flexible catheters have been used to place various objects within the vessels of the human body. Such devices include dilatation balloons, radiopaque markers, liquid medications and various types of occlusion devices such as balloons and embolic coils. Occlusion devices including embolic coils can be used to treat aneurysms or to occlude the blood vessel at a target location.

Coils which are placed in vessels may take the form of helically wound coils, or alternatively, may be randomly wound coils, convoluted coils, coils wound within other coils or many other such configurations to better occlude a blood vessel. Embolic coils are generally formed of radiopaque biocompatible metallic materials, such as platinum, gold, tungsten, or alloys of these metals. The coils can be coated with various materials to improve thrombogenicity. Often times, several coils are placed at a given location in order to occlude the flow of blood through the vessel by promoting thrombus formation at the particular location. The decreased blood flow reduces the pressure on the aneurysm and reduces the risk of a ruptured.

In the past, embolic coils have been placed within the distal end of the catheter. When the distal end of the catheter is properly positioned the coil may then be pushed out of the end of the catheter with, for example, a guidewire to release the coil at the desired location. This procedure of placement of the embolic coil is conducted under fluoroscopic visualization such that the movement of the coil through the vasculature of the body may be monitored and the coil may be placed at the desired location. With these placements systems there is very little control over the exact placement of the coil since the coil may be ejected to a position some distance beyond the end of the catheter.

Patients with potentially life-threatening hemorrhagic brain aneurysms are in need of a safe, reliable, accurate, and fast release mechanism for the deposition of embolic coils via catheters. Numerous procedures have been developed to enable more accurate positioning of coils within a vessel. One commercial product of current use is the Guglielmi Detachable Coil (GDC). The GDC utilizes the electrolytical dissolution of a designated guidewire junction to generate the release action. This procedure typically takes 10-30 minutes and is difficult to control in a reliable fashion. The effects of the dissolved material in the blood stream create a potential hazard to the patient. Problems that have been associated with the release of the coil include the force of the coil exiting the delivery catheter causing the coil to overshoot the desired site or dislodge previously deployed coils. Thus, even with the numerous prior efforts to develop miniature actuators for catheter-based therapeutic application, there remains a need for safe, fast release actuator mechanisms for the delivery of embolic coils, for example.

Another problem with embolic coil delivery systems that rely on a stiff pusher wire extending through the entire length of the catheter to push an element out of the distal end of the catheter is that the pusher wire inherently causes the catheter to be very stiff with the result that it is very difficult to guide the catheter through the vasculature of the body. Accordingly, there is a need for a mechanism for deploying embolic coils from the distal end of a catheter having a flexible body.

There is also a need for precise therapeutic actuators configured to deploy therapeutic elements or devices, e.g. embolic coils, within the narrow confines of blood vessels in the human brain, e.g. 250-500 micrometers in diameter. The present invention satisfies these and other needs.

SUMMARY OF THE INVENTION

Briefly and in general terms, the present invention provides for a release mechanism, a therapeutic actuator, or a system for delivering a therapeutic element or device to a target location. The target location is a site within the vasculature of the human body, for example, a blood vessel in the brain in order to treat an aneurysm.

In its most basic form, the release mechanism includes a therapeutic element, such as an embolic coil, secured to a heating/delivery system through a polymer tether. Upon sufficient heat transfer to from the heating/delivery system to the polymer tether the connection between the heating/delivery system and the therapeutic element is severed. This severance may occur through a melting of the polymer tether which causes the connected coil to break free and disengage from the heating/delivery system. Or, severance of the connection between the therapeutic element and the heating/delivery system through the polymer tether may occur by the tether undergoing a phase transformation that causes it to deform in a manner that releases it from engagement with the connector element securing it to the heating/delivery system. For example, if one end of the polymer tether is enlarged to retain itself in position through a hole in the connector element, heating the polymer tether may cause the enlarged region to narrow and slide through the hole in the connector element, thereby releasing the therapeutic element from the heating/delivery system.

DETAILED DESCRIPTION OF THE PREFERRED EMBODIMENTS

Figure 1:
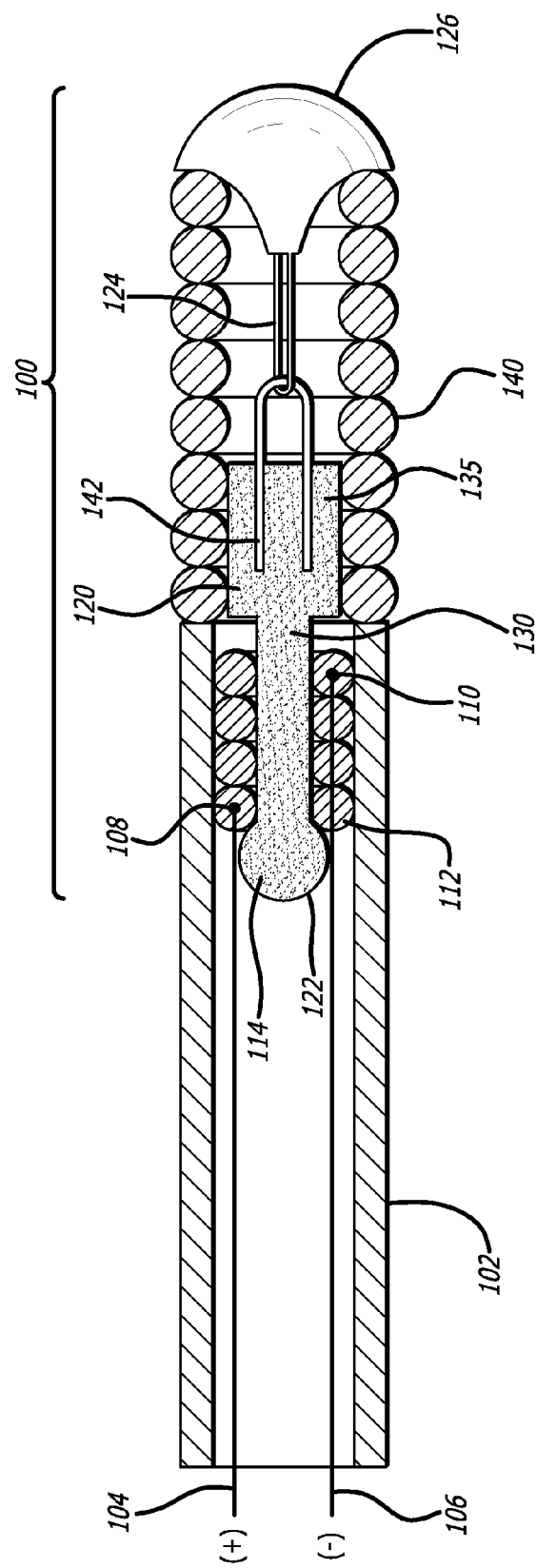
FIG. 1 is a cross sectional view of a system for delivery of a therapeutic device in accordance with an embodiment of the present invention with the therapeutic device in a first retained configuration.

Referring to the drawings, which are provided by way of example, and not by way of limitation, the present invention provides for a therapeutic element delivery system 100 (which may also be referred to as a therapeutic actuator or a release mechanism) including a flexible tube 102 for delivering a therapeutic element 140 to a target site within a body and a polymeric element 122 including a tether portion 130 that may be thermally severed, the polymeric element 122 securing the therapeutic element 140 to the flexible tube 102. The therapeutic element 140 may be an embolic coil or another occlusive device that serves to occlude an aneurysm by filling the aneurysm pouch, creating a physical barrier to reduce blood flow into the aneurysm, and inducing thrombosis or clotting therein. The tube 102 may be flexible along its entire length or the flexible region may be restricted to the distal end of the tube.

The therapeutic element 140 is secured to the flexible tube 102 through a polymeric element 122 that includes a tether portion 130. According to one of several embodiments, the polymeric element 122 is part of a secure and release system that may also include a bulb 114, a tether portion 130, an aggregate portion 135, an anchor 142, a stretch resistant member 124, and a distal bead 126. The interconnection of these elements is discussed below.

The capability of the tether portion 130 to be thermally decoupled to deploy the therapeutic element is beneficial in that is allows prompt precise placement of the therapeutic element at the target site. Whereas prior art devices have relied upon pusher wires and other ejection mechanisms that exert an often uncontrollable and unpredictable force on the therapeutic element to deploy it, the thermally activated tether portion can be quickly and easily decoupled without propelling the therapeutic element out of the delivery tube. This is desirable as uncontrolled therapeutic elements that shoot out of the tube may result in inaccurately placed coils or coils that dislodge other previously placed coils.

Within the flexible tube at least one electrical conductor is provided. For example, there may be a positively charged electrical conductor 104 and a negatively charged electrical conductor 106. The electrical conductors are attached to a thermally responsive element 112 or heating element through attachment points 108, 110. A bulb 122 may also be provided to secure a tether portion 130 of a polymeric element 122 to the thermally responsive element 112 and to at least one electrical conductor, thereby enabling the thermally responsive element 112 to transfer heat to the polymeric element 122 through the proximal tether 118.

The polymeric element 122 also includes an aggregate portion 120 connected to an anchor 142. For example, the anchor 142 may be U-shaped and disposed into the aggregate portion 120 of the polymeric element 122. The anchor 142 may be formed of metal or another material resistant to deformation at the temperature that causes deformation of the polymeric element 122. The anchor 142 and at least the aggregate portion 120 of the polymeric element 122 are disposed within an internal lumen of the therapeutic element 140. The anchor 142 may be secured to the aggregate portion 120 in the molding process of the polymeric element 122 in the molding process, or it may be affixed by adhesives, solder, or welding.

Figure 2:
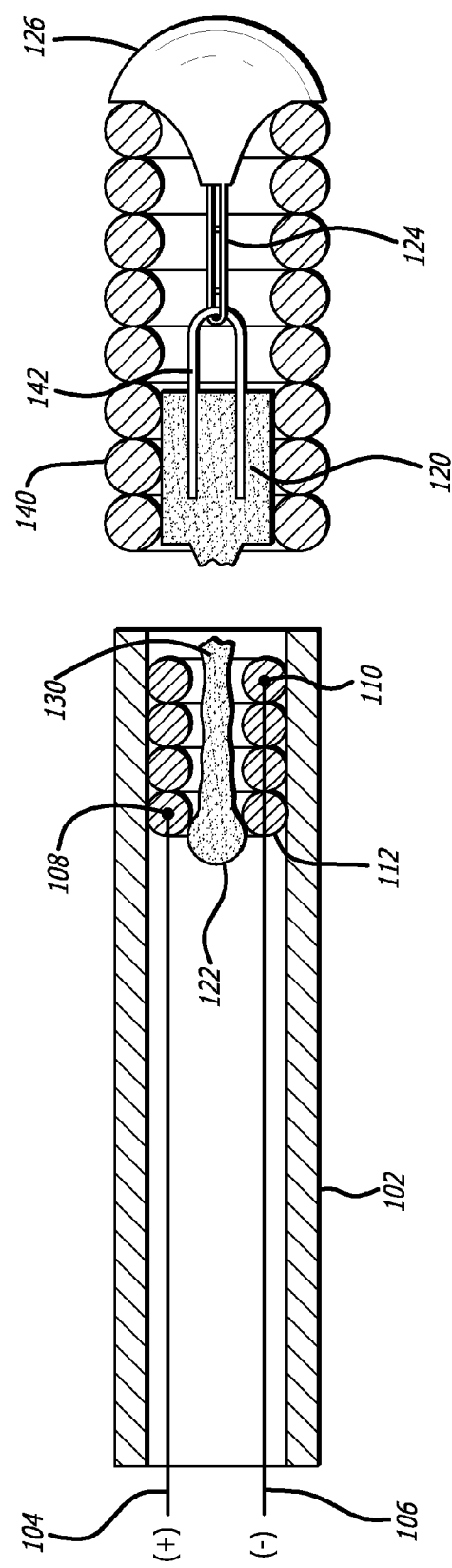
FIG. 2 is a cross sectional view of a system for delivery of a therapeutic device in accordance with an embodiment of the present invention with the therapeutic device in a second deployed configuration.

The anchor 142 is connected to a stretch resistant member 124 at its distal end. For example, the stretch resistant member 124 may loop through a U-shaped anchor 142. The stretch resistant member 124 is attached to a bead 126 at its distal end. The bead 126 holds the therapeutic element 140 as shown in FIG. 1 in which the therapeutic element 140 is retained in the delivery tube 102. A distal outer surface of the bead may be substantially hemispherical, curved, or rounded so as to facilitate an atraumatic introduction of the therapeutic element 140. The stretch resistant member 124 may, but need not, be integrally formed with the distal bead 126. When the tether portion 130 is heated by the heating element 112, the tether weakens and narrows as it melts until it breaks. When the tether portion 130 breaks, the tension in the polymeric element that holds the therapeutic element 140 is released as seen in FIG. 2 and therapeutic element 140 along with its associated bead 126 is released into the patient's body.

The heating of the tether portion 130 by the heating element 112 may sever the connection between the therapeutic element 140 and flexible tube 102 in various ways. For example, according to one embodiment, the tether may be formed of a polymeric material that melts and splits into two or more sections thereby disengaging from the connector that secures it to the heating/delivery system. As another example, according to another embodiment, the tether has a bulb on the proximal end 114 that, when heated, my shrink to the point where it can slide through the heating element 112, releasing the therapeutic element 140. The change in shape of the bulb 114 induces the tether 130 to release itself from flexible tubing 102 and position the therapeutic element 140 at the desired location.

The material used to form the tether portion 130 (and/or bulb 114) of the polymeric element 122 is designed to melt, split, or undergo a phase transformation at a temperature sufficiently above normal body temperature and febrile temperatures so that it is not prematurely activated. The heat necessary to achieve this higher decoupling temperature can be supplied by an auxiliary electrical heating system or an alternative energy source. For example, there may be electrical conductors 104, 106 and a resistive heating coil 112 disposed within the body of the flexible delivery tube. Alternatively, there may be a laser or optical fiber (not shown) in the tube in thermal communication with the polymeric tether 130.

Preferably, the polymeric element 122 and distal bead 126 are formed of non-toxic, biocompatible materials that may also be biodegradable, bioabsorbable or bioerodible such that when they are released as a result of the decoupling with the flexible tubing 102 they do not pose a hazard from being ejected into the bloodstream.

According to one of several embodiments, the therapeutic element delivery system as described herein is capable of operating in small (250-500 micrometers) diameter applications, such as in veins in the human brain, which enables catheter-based devices to reach and treat an aneurysm in the brain.

It will be apparent from the foregoing that while particular forms of the invention have been illustrated and described, various modifications can be made without departing from the spirit and scope of the invention. Accordingly, it is not intended that the invention be limited, except as by the appended claims.

I claim:

1. A therapeutic actuator, comprising a polymeric element having a tether portion that secures a therapeutic element to a heating and delivery system, further comprising:
    a flexible tube defining a lumen therein wherein the therapeutic element is configured to fit adjacent the lumen of the flexible tube and to be released at a distal end of the flexible tube;
    the heating and delivery system comprising an electrical conductor disposed within the lumen of the flexible tube and a resistive heating element also disposed within the lumen of the flexible tube distal to the electrical conductor and electrically connected to the electrical conductor;
    the polymeric element further comprising an aggregate portion, wherein the tether portion is adjacent to the resistive heating element and the aggregate portion is positioned inside the therapeutic element and distal to the tether portion;
    an anchor disposed in the aggregate portion of the polymeric element; and
    a bead disposed on a distal end of the therapeutic element that maintains the therapeutic element in a first configuration through a stretch resistant member that secures the bead to the anchor.

2. The therapeutic actuator of claim 1, wherein the therapeutic actuator is configured such that melting the polymeric element through energy supplied by the electrical conductor that heats the resistive heating element results in the tether portion breaking to deploy the therapeutic element at the distal end of the flexible tube.

3. The therapeutic actuator of claim 1, wherein the anchor has a horseshoe shape.

4. The therapeutic actuator of claim 1, wherein a distal face of the bead has a hemispherical shape.

5. The therapeutic actuator of claim 1, wherein a distal face of the bead has a rounded outer surface that facilitates atraumatic introduction of the therapeutic element.

6. The therapeutic actuator of claim 1, wherein the therapeutic element is an embolic coil configured for treatment of aneurysm.

* * * * *